United States Patent
Zimmer

(10) Patent No.: US 10,626,364 B2
(45) Date of Patent: Apr. 21, 2020

(54) METHOD FOR INCREASING THE GLUTATHIONE LEVEL IN CELLS

(71) Applicant: Merck Patent GmbH, Darmstadt (DE)

(72) Inventor: Aline Zimmer, Gross-Gerau (DE)

(73) Assignee: Merck Patent GmbH, Darmstadt (DE)

( * ) Notice: Subject to any disclaimer, the term of this patent is extended or adjusted under 35 U.S.C. 154(b) by 29 days.

(21) Appl. No.: 15/748,314

(22) PCT Filed: Jul. 1, 2016

(86) PCT No.: PCT/EP2016/001118
§ 371 (c)(1),
(2) Date: Jan. 29, 2018

(87) PCT Pub. No.: WO2017/016631
PCT Pub. Date: Feb. 2, 2017

(65) Prior Publication Data
US 2018/0216061 A1 Aug. 2, 2018

(30) Foreign Application Priority Data
Jul. 30, 2015 (EP) ..................... 15179065

(51) Int. Cl.
*C12N 5/00* (2006.01)
(52) U.S. Cl.
CPC ........ *C12N 5/0018* (2013.01); *C12N 2500/32* (2013.01)
(58) Field of Classification Search
CPC ................................. C12N 2500/32
See application file for complete search history.

(56) References Cited

U.S. PATENT DOCUMENTS

| | | |
|---|---|---|
| 5,208,249 A | 5/1993 | Rowe |
| 5,747,459 A | 5/1998 | Rowe |
| 2011/0077303 A1 | 3/2011 | Sekhar |
| 2013/0338165 A1 | 12/2013 | Baker |
| 2014/0100283 A1 | 4/2014 | Mahoney |

FOREIGN PATENT DOCUMENTS

AU 652988 B 9/1994

OTHER PUBLICATIONS

Suzuki et al., Agric. Bio. Chem., 1980, 44(8):1995-1997.*
Shojaosadati et al., Iranisn J of Biotechnology, 2008, 6(2):63-84.*
International Search Report PCT/EP2016/001118 dated Aug. 4, 2016.
Takeshi Nakatani et al.: "Enhancement of thioredoxin/glutaredoxin-mediated L-cysteine synthesis from S-sulfocysteine increases L-cysteine production in *Escherichia coli*", Microbial Cell Factories, Biomed Central, GB, vol. 11, No. 1, May 18, 2012 (May 18, 2012), pp. 62, XP021129015, ISSN: 1475-2859.
J.S. Church; D.J. Evans, Spectrochimica Acta Part A, vol. 69, 2008, pp. 256-262.
I.H.Segel; M.J.Johnson, Analytical Biochemistry, vol. 5, 1963, pp. 330-337.
R. Banerjee: "Redox outside the Box: Linking Extracellular Redox Remodeling with Intracellular Redox Metabolism", Journal of Biological Chemistry, vol. 287, No. 7, Feb. 10, 2012 (Feb. 10, 2012), US, pp. 4397-4402, XP055291492, ISSN: 0021-9258, DOI: 10.1074/jbc.R111.287995.

* cited by examiner

*Primary Examiner* — Bin Shen
(74) *Attorney, Agent, or Firm* — Millen, White, Zelano & Branigan, PC

(57) ABSTRACT

The present invention relates to the use of sulfocysteine and derivatives thereof to increase the gluthathione pool in cells.

11 Claims, 3 Drawing Sheets

METHOD FOR INCREASING THE GLUTATHIONE LEVEL IN CELLS

The present invention relates to the use of sulfocysteine and derivatives thereof to increase the glutathione pool in cells.

Glutathione, a tri-peptide molecule consisting of the amino acids L-glycine, L-cysteine, and L-glutamic acid (also known as L-glutamate), is one of the major intracellular antioxidant in mammalians.

Glutathione exists in reduced (GSH) and oxidized (GSSG) states, with the reduced form (GSH) predominating. An increased GSSG-to-GSH ratio is considered indicative of oxidative stress.

Although glutathione is produced in most cells, many diseases and other pathologies are associated with reduced levels of intracellular glutathione. Glutathione is a tightly regulated intracellular constituent, and is limited in its production by negative feedback inhibition of its own synthesis through the enzyme gamma-glutamylcysteine synthetase, thus greatly minimizing any possibility of overdosage. Glutathione augmentation using precursors of glutathione synthesis is a strategy developed to address states of glutathione deficiency, high oxidative stress, immune deficiency, and xenobiotic overload in which glutathione plays a part in the detoxification of the xenobiotic in question. Glutathione deficiency states in humans include, but are not limited to, HIV/AIDS, chemical and infectious hepatitis, myalgic encephalomyelitis chronic fatigue syndrome, prostate and other cancers, cataracts, Alzheimer's disease, Parkinson's disease, chronic obstructive pulmonary disease, asthma, radiation poisoning, malnutritive states, arduous physical stress, and aging, and has been associated with suboptimal immune response. Many clinical pathologies are associated with oxidative stress and are elaborated upon in numerous medical references.

Moreover, it is recognized generally that deficiencies in the glutathione system lead to significant cellular aging, and, ultimately, cellular morbidity. The concentration of cellular glutathione has a significant effect on antioxidant function; and nutrient limitation, exercise and oxidative stress have significant effects on cellular glutathione concentrations.

Glutathione is synthesized in a series of biochemical reactions utilizing ATP, magnesium and the three amino acids glycine, glutamate and cysteine. In general, the rate of synthesis of gamma-glutamylcysteine determines the rate of synthesis of glutathione, and the sulfhydryl group of cysteine provides glutathione with its biological potency. Thus, the cysteine availability is essential for the availability of glutathione and its antioxidant function.

The availability of glutathione can be relevant for therapeutic applications and cosmetic applications but also for cell culture applications. An increase of the total GSH pool in cultured cells leads to a decreased oxidative reactivity in the intracellular compartment and thus to a prolonged culture duration and often also to an increase in titer.

The aim of the present invention was thus to find a way to increase the GSH content of cells. Several approaches for this, mainly in the therapeutic area, are known in the art.

US 2014/0100283 discloses the use of the GSH derivative S-acetyl-glutathion.

US 2011/0077303 discloses providing glycine and N-acetyl-cysteine.

US 2013/0338165 suggests the use of certain cysteine/cysteine prodrugs or N-acetyl-cysteine prodrugs.

For cell culture applications, such approaches have only limited feasibility as the glutathione precursors are often not taken up by the cells because of the requirement of a specific transporter system. For cell culture, a more effective and universal approach would be favorable.

It has been found that S-sulfocysteine and salts thereof increase the GSH content of mammalian cells. It has been found in addition that if cells are provided with equivalent amounts of either cysteine or S-sulfocysteine, the cells having received s-sulfocysteine show a higher amount of GSH compared to the cells with cysteine.

This invention is consequently directed to a method for increasing the level of glutathione in cells comprising adding to said cells S-sulfocysteine and/or a S-sulfocysteine salt in an amount effective to increase the intracellular glutathione level.

In a preferred embodiment, the method is performed by culturing said cells in a liquid cell culture medium and adding to the cell culture medium at one or more points in time in the course of the culture S-sulfocysteine and/or a S-sulfocysteine salt in an amount effective to increase the intracellular glutathione level of the cells in culture.

In a preferred embodiment (S)-2-amino-3-sulfosulfanyl-propanoic acid sodium salt is added.

In another preferred embodiment the cell culture medium has a pH of between 6.8 and 7.5.

In another preferred embodiment, S-sulfocysteine and/or a S-sulfocysteine salt are added in an amount so that their concentration in the cell culture is between 0.4 and 50 mM.

In one embodiment, the cells are cultured in a cell culture medium comprising at least one or more saccharide components, one or more amino acids, one or more vitamins or vitamin precursors, one or more salts, one or more buffer components, one or more co-factors and one or more nucleic acid components.

In one embodiment, the method of the present invention is performed by
 a) providing a bioreactor
 b) mixing the cells to be cultured with a cell culture medium comprising S-sulfocysteine and/or a S-sulfocysteine salt
 c) incubating the mixture of step b).

In another, preferred embodiment, the method of the invention is performed by
 Filling into a bioreactor cells and a liquid cell culture medium
 Incubating the cells in the bioreactor
 Continuously over whole time of the incubation of the cells in the bioreactor or once or several times within said incubation time adding a cell culture medium, which is in this case a feed medium, to the bioreactor whereby the feed medium comprises S-sulfocysteine and/or a S-sulfocysteine salt.

Preferably the feed medium comprises S-sulfocysteine and/or a S-sulfocysteine salt in a concentration between 1 and 100 mmol/l, preferably between 5 and 20 mmol/l.

The present invention is further directed to the use of S-sulfocysteine and/or a S-sulfocysteine salt for increasing the intracellular amount of glutathione.

Figure 1:
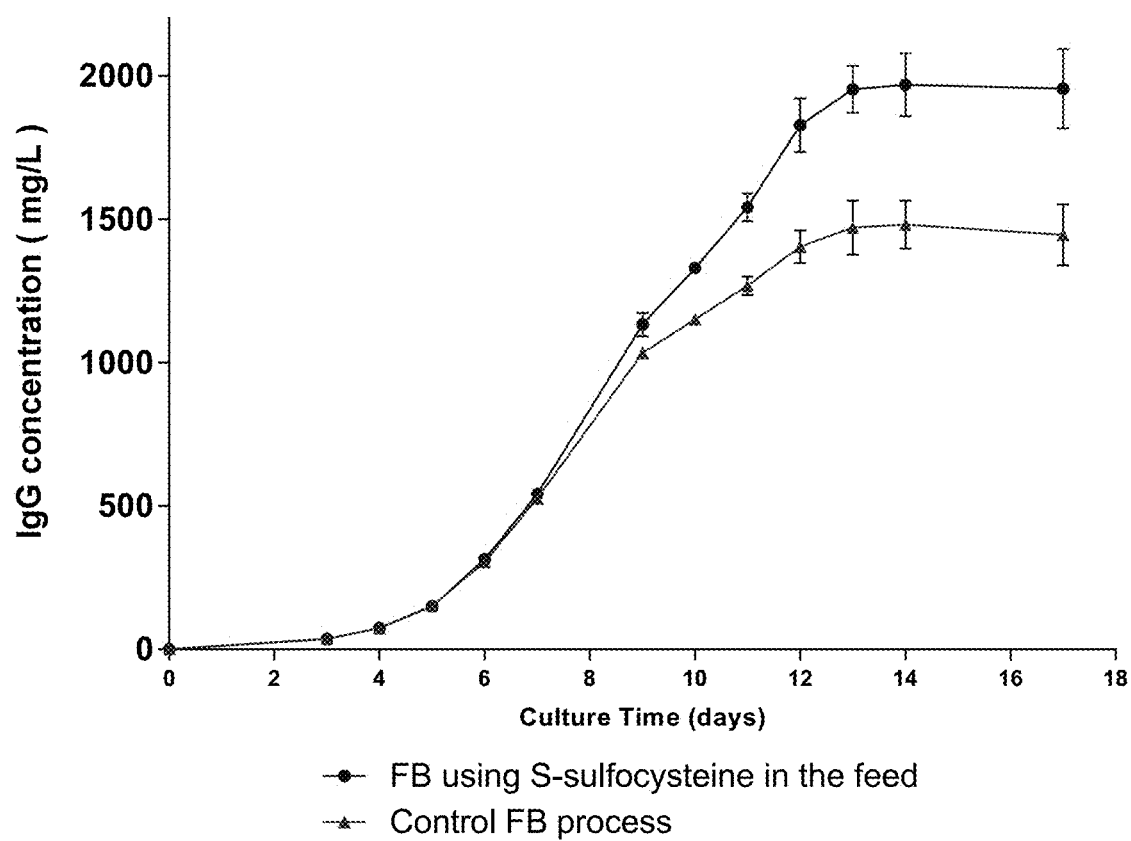
FIG. 1 shows a comparison of the IgG concentrations achieved with CHO cells cultured in a bioreactor fed-batch experiment with either cysteine or S-sulfocysteine. Further details can be found in the Examples.

S-sulfocysteine, also called (S)-2-amino-3-sulfosulfanyl-propanoic acid is a product e.g. obtainable by the condensation of sulfuric acid and cysteine. Suitable salts are alkaline metal or alkaline earth metal salts, e.g. the lithium salts, the sodium salts, the potassium salts, the calcium salts or the magnesium salts or mixtures thereof. Preferred are sodium salt, the potassium salt, the calcium salt and the magnesium salt, most preferred is the sodium salt.

S-sulfocysteine and its salts can also be shown by the following formula I and II:

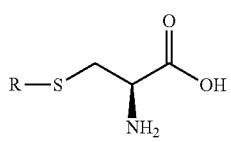

with R being

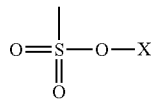

and X being H, Li, Na, K, ½ Ca, ½ Mg, preferably H, Na, K. The term propanoic acid can also be used instead of the term propionic acid.

The synthesis of 2-Amino-3-sulfosulfanyl-propionic acid, also called (S)-2-Amino-3-sulfosulfanyl-propanoic acid, S-sulfo-cysteine or cysteine-S-sulfate, and its salts is disclosed for example in I. H. Segel and M. J. Johnson, Analytical Biochemistry 5 (1963), 330-337 and J. S. Church, D. J. Evans, Spectrochimica Acta Part A 69 (2008) 256-262. The sodium salt is further commercially available from Bachem, Switzerland.

A cell culture medium is any mixture of components which maintains and/or supports the in vitro growth of cells. It might be a complex medium or a chemically defined medium. The cell culture medium can comprise all components necessary to maintain and/or support the in vitro growth of cells or only some components so that further components are added separately. Examples of cell culture media are full media which comprise all components necessary to maintain and/or support the in vitro growth of cells as well as media supplements or feeds. A full medium also called base medium typically has a pH between 6.8 and 7.8. A feed medium preferably has a pH below 8.5.

Typically, the cell culture media according to the invention are used to maintain and/or support the growth of cells in a bioreactor and to support the IgG production of said cells.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. They are manufactured for the purpose of dissolving in water and/or aqueous solutions and in the dissolved state are designed, often with other supplements, for supplying cells with a substantial nutrient base for growth and/or production of biopharmaceuticals from said cells.

Most biopharmaceutical production platforms are based on fed-batch cell culture protocols. The aim typically is to develop high-titer cell culture processes to meet increasing market demands and reduce manufacturing costs. Beside the use of high-performing recombinant cell lines, improvements in cell culture media and process parameters are required to realize the maximum production potentials In a fed-batch process, a base medium supports initial growth and production, and a feed medium prevents depletion of nutrients and sustains the production phase. The media are chosen to accommodate the distinct metabolic requirements during different production phases. Process parameter settings—including feeding strategy and control parameters—define the chemical and physical environments suitable for cell growth and protein production.

A feed or feed medium is a cell culture medium which is not the basal medium that supports initial growth and production in a cell culture but the medium which is added at a later stage to prevent depletion of nutrients and sustains the production phase. A feed medium can have higher concentrations of some components compared to a basal culture medium. For example, some components, such as, for example, nutrients including amino acids or carbohydrates, may be present in the feed medium at about 5×, 6×, 7×, 8×, 9×, 10×, 12×, 14×, 16×, 20×, 30×, 50×, 100×, 200×, 400×, 600×, 800×, or even about 1000× of the concentrations in a basal medium.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts or digests or other components which may contribute chemically poorly defined proteins to the media. Chemically undefined or poorly defined chemical components are those whose chemical composition and structure is not known, are present in varying composition or could only be defined with enormous experimental effort—comparable to the evaluation of the chemical composition and structure of a protein like albumin or casein.

A powdered cell culture medium or a dry powder medium is a cell culture medium typically resulting from a milling process or a lyophilisation process. That means the powdered cell culture medium is a granular, particulate medium—not a liquid medium. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated. A powdered cell culture medium can also be a granulated cell culture medium, e.g. dry granulated by roller compaction.

Powdered cell culture media are preferably produced by mixing all components and milling them. The mixing of the components is known to a person skilled in the art of producing dry powdered cell culture media by milling.

Preferably, all components are thoroughly mixed so that all parts of the mixture have nearly the same composition. The higher the uniformity of the composition, the better the quality of the resulting medium with respect to homogenous cell growth.

The milling can be performed with any type of mill suitable for producing powdered cell culture media. Typical examples are ball mills, pin mills, fitz mills or jet mills. Preferred is a pin mill, a fitz mill or a jet mill, very preferred is a pin mill.

A person skilled in the art knows how to run such mills.

For use of the milled powdered media a solvent, preferably water (most particularly distilled and/or deionized water or purified water or water for injection) or an aqueous buffer is added to the media and the components are mixed until the medium is totally dissolved in the solvent.

The solvent may also comprise saline, soluble acid or base ions providing a suitable pH range (typically in the range between pH 1.0 and pH 10.0), stabilizers, surfactants, preservatives, and alcohols or other polar organic solvents.

It is also possible to add further substances like buffer substances for adjustment of the pH, fetal calf serum, sugars etc., to the mixture of the cell culture medium and the solvent. The resulting liquid cell culture medium is then contacted with the cells to be grown or maintained.

Cells to be treated with the method according to the present invention may be normal cells, immortalized cells, diseased cells, transformed cells, mutant cells, somatic cells, germ cells, stem cells, precursor cells or embryonic cells, any of which may be established or transformed cell lines or obtained from natural sources. Preferably, the cells are mammalian cells, more preferred BHK, VERO, HEK or CHO cells, most preferred are CHO-S, CHO dhfr- (DG44 and Duxb11), CHO-M and CHOK1 cells.

Cell culture media, especially the full media, typically comprise at least one or more saccharide components, one or more amino acids, one or more vitamins or vitamin precursors, one or more salts, one or more buffer components, one or more co-factors and one or more nucleic acid components.

The media may also comprise sodium pyruvate, insulin, vegetable proteins, fatty acids and/or fatty acid derivatives and/or pluronic acid and/or surface active components like chemically prepared non-ionic surfactants. One example of a suitable non-ionic surfactant are difunctional block copolymer surfactants terminating in primary hydroxyl groups also called poloxamers, e.g. available under the trade name pluronic® from BASF, Germany.

Saccharide components are all mono- or di-saccharides, like glucose, galactose, ribose or fructose (examples of monosaccharides) or sucrose, lactose or maltose (examples of disaccharides).

Examples of amino acids according to the invention are tyrosine, the proteinogenic amino acids, especially the essential amino acids, leucine, isoleucine, lysine, methionine, phenylalanine, threonine, tryptophane and valine, as well as the non-proteinogenic amino acids like D-amino acids.

Tyrosine means L- or D-tyrosine, preferably L-tyrosine.

Cysteine means L- or D-cysteine, preferably L-cysteine.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are Copper(II) sulphate pentahydrate ($CuSO_4.5H_2O$), Sodium Chloride (NaCl), Calcium chloride ($CaCl_2.2H_2O$), Potassium chloride (KCl), Iron(II)sulphate, sodium phosphate monobasic anhydrous ($NaH_2PO_4$), Magnesium sulphate anhydrous ($MgSO_4$), sodium phosphate dibasic anhydrous ($Na_2HPO_4$), Magnesium chloride hexahydrate ($MgCl_2.6H_2O$), zinc sulphate heptahydrate.

Examples of buffers are $CO_2/HCO_3$ (carbonate), phosphate, HEPES, PIPES, ACES, BES, TES, MOPS and TRIS.

Examples of cofactors are thiamine derivatives, biotin, vitamin C, NAD/NADP, cobalamin, flavin mononucleotide and derivatives, glutathione, heme nucleotide phosphates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

Feed media may have a different composition compared to full media. They typically comprise amino acids, trace elements and vitamins. They might also comprise saccharide components but sometimes for production reasons the saccharide components are added in a separate feed.

A suitable feed medium might for example comprise one or more of the following compounds:

L-ASPARAGINE MONOHYDRATE
L-ISOLEUCINE
L-PHENYLALANINE
SODIUM L-GLUTAMATE MONOHYDRATE
L-LEUCINE
L-THREONINE
L-LYSINE MONOHYDROCHLORIDE
L-PROLINE
L-SERINE
L-ARGININE MONOHYDROCHLORIDE
L-HISTIDINE MONOHYDROCHLORIDE MONOHYDRATE
L-METHIONINE
L-VALINE
MONO-SODIUM-L-ASPARTATE-MONOHYDRATE
L-TRYPTOPHAN
CHOLINE CHLORIDE
MYO-INOSITOL
NICOTINAMIDE
CALCIUM-D(+) PANTOTHENATE
PYRIDOXINE HYDROCHLORIDE
THIAMINE CHLORIDE HYDROCHLORIDE
VITAMIN B12 (CYANOCOBALAMINE) MICRONIZED
BIOTIN
FOLIC ACID
RIBOFLAVIN
MAGNESIUM SULFATE ANHYDROUS
COPPER(II) SULFATE PENTAHYDRATE
ZINC SULFATE HEPTAHYDRATE
1,4-DIAMINOBUTANE DIHYDROCHLORIDE
AMMONIUM HEPTAMOLYBDATE TETRAHYDRATE

CADMIUM SULFATE HYDRATE
MANGANESE(II) CHLORIDE TETRAHYDRATE
NICKEL(II) CHLORIDE HEXAHYDRATE
SODIUM META SILICATE
SODIUM METAVANADATE
TIN(II) CHLORIDE DIHYDRATE
SODIUM SELENITE (ABOUT 45% SE)
SODIUM DIHYDROGEN PHOSPHATE MONOHYDRATE
AMMONIUM IRON(III) CITRATE (ABOUT 18% FE)

The gist of the present invention is to increase the total glutathione pool in cells. It has been found that by increasing the amount of glutathione in cells by adding S-sulfocysteine and/or its salts one or more of the following positive effects are typically achieved:

Longer culture duration
Higher titer (concentration of the produced IgG)
Higher specific productivity
Lower intracellular oxidative potential Those effects are very beneficial for cell culture as high titer, high productivity and also longer culture duration all increase cell culture efficiency.

The cells to be treated with S-sulfocysteine and/or its salts according to the invention are typically cells that are cultured in a bioreactor for biopharma production purposes. Examples of suitable cell culture processes are fed batch processes or perfusion cell culture processes.

S-sulfocysteine and/or its salts can be added to the cells at any stage of the cell culture.

It can be added when starting the cell culture. In this case, S-sulfocysteine and/or its salts are preferably mixed and milled with the other ingredients of the base medium which is used to start the cell culture. This dry powder mixture comprising S-sulfocysteine and/or its salts is then dissolved in a suitable solvent by admixing the powder and the solvent such that the powder dissolves and produces a liquid cell culture medium with a desired and homogenous concentration of the media components.

S-sulfocysteine and/or its salts can also be added one or more times during the culturing of the cells. A cell culture is typically performed for 1 to 3 weeks. During this time feed medium is added either continuously or one or more times. S-sulfocysteine and/or its salts can be added in a feed medium together with other feed medium ingredients or it can be added in a separate feed which only comprises S-sulfocysteine and/or its salts. Also the feed is typically a liquid so that all components of the feed dissolved in a suitable solvent prior to the addition to the cell culture.

In a preferred embodiment, S-sulfocysteine and/or its salts are added as feed. It is preferably added at least 4 times during cell culture, preferably between 4 and 6 times.

In one embodiment, S-sulfocysteine and/or its salts is added between every second and every fourth day.

The pH of the feed comprising S-sulfocysteine and/or its salts is preferably between 6.8 and 7.5, most preferred between 6.8 and 7.1.

It has been found that the level of glutathione can be most effectively increased if S-sulfocysteine and/or its salts are present in the cell culture in concentrations between 0.4 and 50 mM, preferably between 1 and 10 mM. Typically the volume of the feed that is added to the cell culture during the whole culture process is about 30% of the volume of the cell culture medium which is already present in the bioreactor. The concentration of S-sulfocysteine and/or its salts in the feed are preferably between 1 and 100 mmol/l, preferably between 5 and 20 mmol/l.

Typically a cell culture is performed by
a) providing a bioreactor
b) mixing the cells to be cultured with a liquid cell culture medium in the bioreactor
c) incubating the mixture of step b) for a certain time A bioreactor is any container, bag, vessel or tank in which cells can be cultured. Performing a cell culture is known to a person skilled in the art. This is typically done by incubating the cells in the bioreactor under suitable conditions like pH, osmolality, temperature, agitation, aeration (oxygen/$CO_2$) etc. and the optional addition of feed media one or several times during the cell culture. Preferably, the cell culture is performed as fed-batch cell culture.

Fed-batch culture is a cell culture process where one or more nutrients (substrates) are fed (supplied) to the bioreactor during cultivation of the cells and in which the product(s) remain in the bioreactor until the end of the run. An alternative description of the method is that of a culture in which a base medium supports the initial cell culture and a feed medium is added to prevent nutrient depletion. The advantage of the fed-batch culture is that one can control concentration of fed-substrate in the culture liquid at arbitrarily desired levels.

Generally speaking, fed-batch culture is superior to conventional batch culture when controlling concentrations of a nutrient (or nutrients) affect the yield or productivity of the desired metabolite, like in this case S-sulfocysteine and/or its salts.

Consequently, preferably, the present invention is performed by

Filling into a bioreactor cells and liquid cell culture medium

Incubating the cells in the bioreactor

Continuously over whole time of the incubation of the cells in the bioreactor or once or several times within said incubation time adding a cell culture medium, which is in this case a feed medium, to the bioreactor whereby the feed medium preferably has a pH between 6.8 and 7.5 and comprises S-sulfocysteine and/or its salts.

In another embodiment, cell culture is performed as perfusion culture. Perfusion culture is a culture by which the cells are restrained in the culture by, e.g., filtration, encapsulation, anchoring to microcarriers, etc., and the culture medium is continuously or intermittently introduced and removed from the bioreactor. S-sulfocysteine and/or its salts are in this case preferably introduced as part of the culture medium.

In perfusion culture, in the course of cell cultivation, the cells (biomass) are separated from the cell culture (cell suspension) and on the one hand the spent medium is withdrawn from the process, and on the other hand new nutrients are made available to the cells through fresh medium. If cells are retained in the culture system during the process, this is called "perfusion". If cells are removed from the system with the spent medium during the process, this is called "continuous method". In perfusion processes, the cells can also be removed from the cultivation system at defined time intervals, so as to be able to maintain a maximum cell concentration. To a person skilled in the art, this operation is known as "bleeding". Cell separation is carried out with various technologies, with some technologies promoting cell separation indirectly. Examples of some possible methods of cell separation are filtration, cell encapsulation, cell adherence to microcarriers, cell sedimentation or centrifugation.

It has been found that with the method of the present invention, the intracellular glutathione level can be effectively increased. Typically, the level can be more than doubled at least part of the time of the cell culture. Preferably, the level of glutathione is increased by at least 10%, preferably more than 25% for more than half of the time of the cell culture compared to a cell culture under equivalent conditions but without the addition of S-sulfocystein and/or its salts.

The present invention is further illustrated by the following figures and examples, however, without being restricted thereto.

The entire disclosure of all applications, patents, and publications cited above and below, as well as of corresponding EP 15179065.6 field Jul. 30, 2015, are hereby incorporated by reference.

EXAMPLES

The following examples represent practical applications of the invention.

Bioreactor Fed-Batch Experiment in Cellvento® CHO 220 Medium and Feed 220 Using a CHO Suspension Cell Line in 1.2 L Glass Bioreactors.

15 mM S-sulfo-L-cysteine (SS) was integrated in the neutral pH main Feed-220 (n=5). Feed was added at 3% (v/v) at day 3 and 6% (v/v) at days 5, 7, 9 and 14. In the control condition, the feed without SS was added at the same ratios whereas 150 mM L-cysteine was added separately in an alkaline feed and added at following ratios 0.3% (v/v) at day 3 and 6% (v/v) at days 5, 7, 9, 14 (n=2). pH was controlled at 6.95+/−0.15. Dissolved oxygen concentration was controlled at 50% air saturation by sparging with pure oxygen and air via an open pipe sparger. Temperature was set at 37° C. and shifted from 37° C. to 33° C. on day 5 of culture. Agitation was maintained at 140 rpm. The IgG concentration in the supernatant was measured using the Cedex BioHT with a turbidometric method. The results are given in FIG. 1. It can be seen that the titer (IgG concentration) is higher with SS compared to standard.

Figure 2:
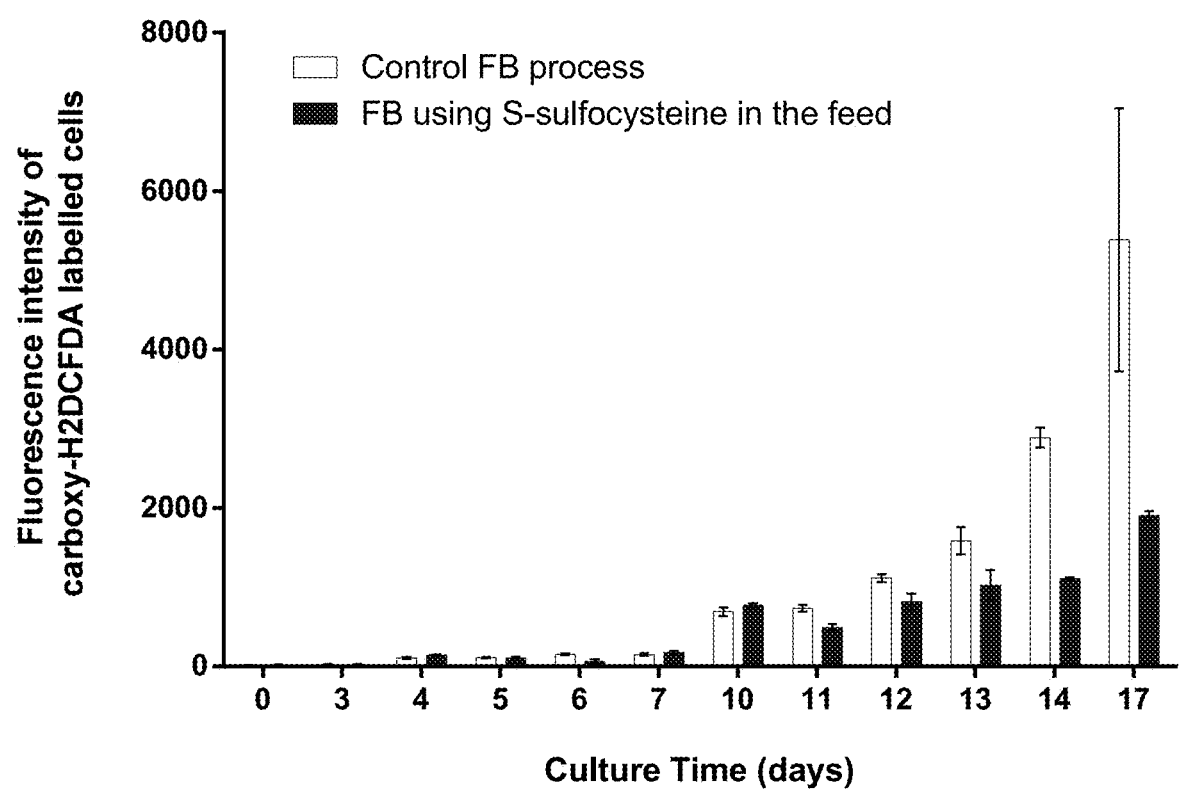
FIG. 2 shows a comparison of the intracellular reactive species of CHO cells cultured in a bioreactor fed-batch experiment with either cysteine or S-sulfocysteine. Further details can be found in the Examples.

Intracellular Reactive Species in CHO Cells in a Fed-Batch Using S-Sulfocysteine Vs the Control Process Intracellular reactive species were quantified using 6-carboxy-2',7'-dichlorodihydrofluorescein diacetate staining (Carboxy $H_2$DCFDA, Life Technologies). The increase in fluorescence due to oxidative reactions was determined using a Perkin Elmer fluorescence reader. For these experiments, measurements were done during fed batch experiments comparing the control condition and 15 mM SSC condition. Samples were taken every day and analyzed immediately. Briefly, $3 \times 10^5$ cells were centrifuged (1200 rpm, 5 min) and either resuspended in PBS (negative control) or loaded with 50 µM Carboxy-$H_2$DCFDA and incubated for 20 min at 37° C. and 1000 rpm. Cells were then centrifuged, resuspended in PBS and analyzed using the plate reader (n=3 for both conditions). The lower fluorescence intensity when using S-sulfocysteine in the feed indicates a lower reactivity in the cells and thus an antioxidative potential of the molecule. The results are shown in FIG. 2.

Figure 3:
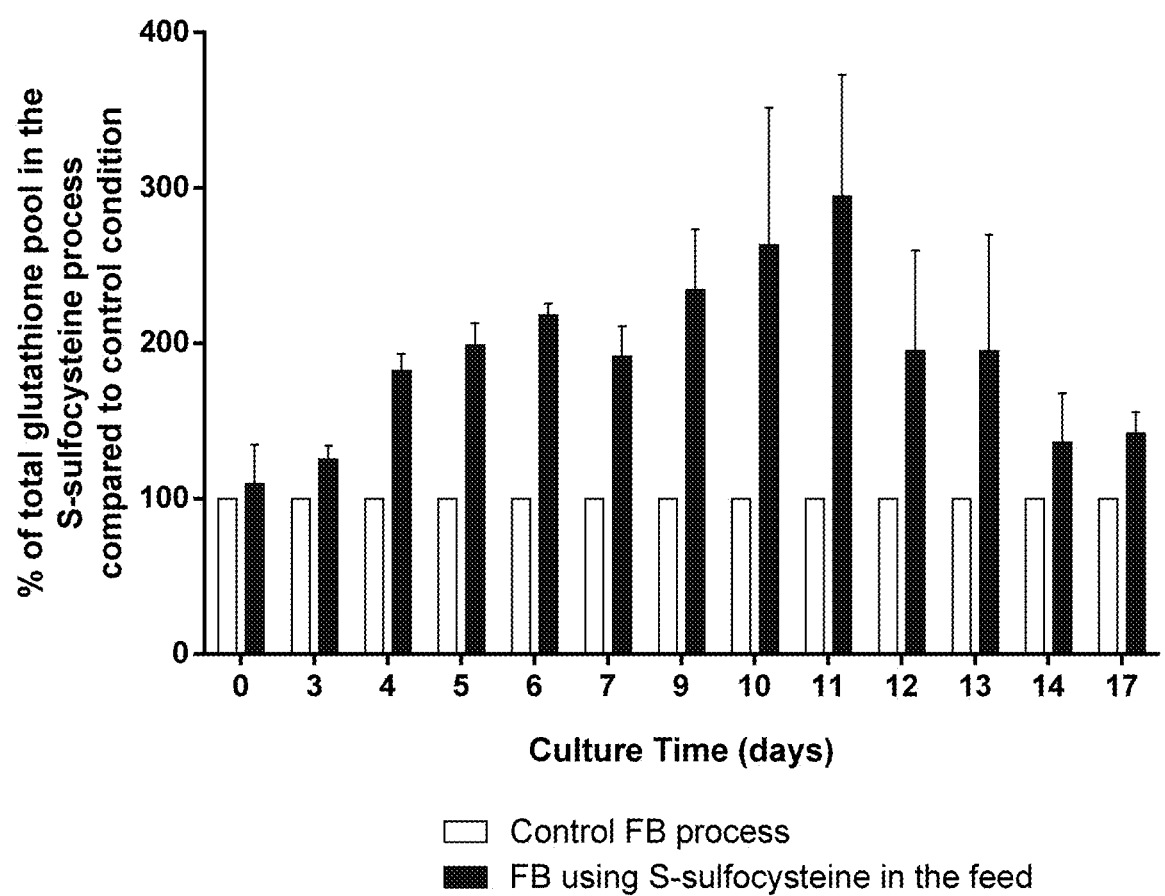
FIG. 3 shows a comparison of the glutathione levels of CHO cells cultured in a bioreactor fed-batch experiment with either cysteine or S-sulfocysteine. Further details can be found in the Examples.

Intracellular Total Glutathione in CHO Cells During a Fed-Batch Using S-Sulfocysteine Vs the Control Process To quantify intracellular total glutathione, cells were washed three times in cold PBS and frozen at −20° C. for further analysis. To inhibit the activity of potential Cys-converting enzymes, $12 \times 10^6$ cells were lysed in 100 µl of phosphoSafe reagent (Merck Millipore) containing four phosphatase inhibitors: sodium fluoride, sodium vanadate, β-glycerophosphate and sodium pyrophosphate and supplemented with 20 mM iodoacetamide (alkylation of all enzyme containing one cysteine in the active site). The glutathione concentrations (GSH and GSSG) were determined via UPLC using a pre-column derivatization relying on AccQ Tag Ultra® reagent kit. Derivatization, chromatography and data analysis were carried out following the supplier recommendations (Waters, Milford, Mass.). Total glutathione was obtained by addition of GSH and GSSG and normalized to the concentration obtained in the control condition each day of the FB process. The results are shown in FIG. 3.

The invention claimed is:

1. A method for increasing the level of glutathione in mammalian cells, comprising adding to said cells an amount of S-sulfocysteine and/or a S-sulfocysteine salt effective to increase the intracellular glutathione level.

2. The method of claim 1, wherein said cells are cultured in a liquid cell culture medium and wherein S-sulfocysteine and/or a S-sulfocysteine salt is added to the cell culture medium at one or more points in time in the course of the culture, in an amount effective to increase the intracellular glutathione level of the cells in culture.

3. The method of claim 2, wherein the cell culture medium has a pH of between 6.8 and 7.5.

4. The method of claim 2, wherein the level of glutathione is increased to more than 25% higher for more than half of the time of the cell culture compared to a cell culture without the addition of S-sulfocysteine and/or its salts.

5. The method of claim 1, wherein (S)-2-amino-3-sulfo-sulfanylpropanoic acid sodium salt is added.

6. The method of claim 1, wherein S-sulfocysteine and/or a S-sulfocysteine salt are added in an amount whereby their concentration in the cell culture is between 0.4 and 50 mM.

7. The method of claim 1, wherein the cells are cultured in a cell culture medium comprising at least one or more saccharide components, one or more amino acids, one or more vitamins or vitamin precursors, one or more salts, one or more buffer components, one or more co-factors and one or more nucleic acid components.

8. The method of claim 1, wherein the method comprises
   a) mixing the cells to be cultured with a cell culture medium comprising S-sulfocysteine and/or a S-sulfocysteine salt in a bioreactor, and
   b) incubating the mixture of step a).

9. The method of claim 1, wherein the method comprises introducing cells and a liquid cell culture medium into a bioreactor,
   incubating the cells in the bioreactor, and
   adding a feed medium to the bioreactor, continuously over the whole time of the incubation of the cells in the bioreactor, or once or several times within said incubation time,
   whereby the feed medium comprises S-sulfocysteine and/or a S-sulfocysteine salt.

10. The method of claim 9, wherein the feed medium comprises S-sulfocysteine and/or a S-sulfocysteine salt in a concentration between 1 and 100 mmol/l.

11. The method of claim 1, comprising adding S-sulfocysteine and/or a S-sulfocysteine salt to cells in culture in an amount effective to increase the intracellular amount of glutathione.

* * * * *